(12) United States Patent
Lindner et al.

(10) Patent No.: US 11,878,492 B2
(45) Date of Patent: Jan. 23, 2024

(54) TACKIFIED HOTMELT ADHESIVE COMPOSITION

(71) Applicant: The Procter & Gamble Company, Cincinnati, OH (US)

(72) Inventors: Torsten Lindner, Kronberg (DE); Matthias Morand, Sulzbach (DE); Christian Neu, Eppstein (DE); Robert Haines Turner, Cincinnati, OH (US); Benedikt Hartmut Hermann Peter Wimmer, Zurich (CH)

(73) Assignee: The Procter and Gamble Company, Cincinnati, OH (US)

( * ) Notice: Subject to any disclaimer, the term of this patent is extended or adjusted under 35 U.S.C. 154(b) by 199 days.

(21) Appl. No.: 17/514,037

(22) Filed: Oct. 29, 2021

(65) Prior Publication Data

US 2022/0135845 A1     May 5, 2022

Related U.S. Application Data (60) Provisional application No. 63/107,492, filed on Oct. 30, 2020.

(51) Int. Cl.

| | |
|---|---|
| *B32B 27/12* | (2006.01) |
| *A61L 15/58* | (2006.01) |
| *B32B 5/02* | (2006.01) |
| *B32B 7/12* | (2006.01) |
| *B32B 37/12* | (2006.01) |
| *C09J 123/14* | (2006.01) |

(52) U.S. Cl.
CPC ............ *B32B 27/12* (2013.01); *A61L 15/585* (2013.01); *B32B 5/022* (2013.01); *B32B 7/12* (2013.01); *B32B 37/1207* (2013.01); *C09J 123/14* (2013.01); *B32B 2037/1215* (2013.01); *B32B 2555/02* (2013.01); *C08L 2205/025* (2013.01); *C08L 2205/03* (2013.01)

(58) Field of Classification Search
CPC ... C09J 123/10; C09J 123/14; C08L 2205/03; C08L 2314/06
See application file for complete search history.

(56) References Cited

U.S. PATENT DOCUMENTS

| | | | |
|---|---|---|---|
| 10,011,744 B2 | 7/2018 | Wang et al. | |
| 2010/0285246 A1* | 11/2010 | Becker | C08L 23/142 |
| | | | 428/17 |
| 2014/0358100 A1† | 12/2014 | Remmers | |
| 2017/0014277 A1* | 1/2017 | Matsui | B32B 37/0076 |
| 2018/0002579 A1 | 1/2018 | Hu | |
| 2019/0144719 A1* | 5/2019 | Wang | B32B 27/12 |
| | | | 156/334 |
| 2019/0321242 A1† | 10/2019 | Turner | |
| 2019/0382630 A1† | 12/2019 | Zhou | |

FOREIGN PATENT DOCUMENTS

| | | | |
|---|---|---|---|
| DE | 102018118105 A1 † | 1/2020 | |
| EP | 3402857 A1 | 11/2018 | |
| WO | WO1994010256 A1 † | 5/1994 | |
| WO | 2018098431 A1 | 5/2018 | |
| WO | 2019094659 A1 | 5/2019 | |

OTHER PUBLICATIONS

PCT Search Report and Written Opinion for PCT/US2021/057164 dated Jan. 26, 2022,15 pages.

\* cited by examiner
† cited by third party

*Primary Examiner* — Jeffrey C Mullis
(74) *Attorney, Agent, or Firm* — Amanda Herman Berghauer; Daniel Albrecht (57) ABSTRACT

A hotmelt composition comprising, a low molecular weight metallocene-catalyzed polymer, a high molecular weight polymer, an amorphous polyolefin and a tackifier. The hotmelt composition is particularly useful in absorbent articles such as diapers. The hotmelt composition provides especially good nonwoven-film bonds but can also be used for nonwoven-nonwoven bonds.

18 Claims, 4 Drawing Sheets

TACKIFIED HOTMELT ADHESIVE COMPOSITION

CROSS-REFERENCE TO RELATED APPLICATIONS

This application claims the benefit, under 35 USC 119(e), to U.S. Provisional Patent Application No. 63/107,492, filed on Oct. 30, 2020 which is herein incorporated by reference in their entirety.

The present invention is directed at a hotmelt adhesive composition that can be used to bond a first substrate to a second substrate. The hotmelt adhesive is useful in absorbent articles such as diapers and provides especially good nonwoven-film bonds, but can also be used for nonwoven-nonwoven bonds. The hotmelt adhesive comprises a blend of polymers having different characteristics and a tackifier.

BACKGROUND

Disposable absorbent articles, such as diapers, training pants or adult incontinence articles, typically comprise a liquid-permeable topsheet, a liquid-impermeable backsheet and an absorbent core located between the topsheet and the backsheet, among other features. The liquid-permeable topsheet is positioned next to the body of the wearer when the disposable article is worn and allows passage of bodily fluids into the absorbent core. The liquid-impermeable backsheet typically comprises a plastic film, which prevents leakage of fluids held in the absorbent core, and optionally a nonwoven outer cover. The absorbent core typically comprises superabsorbent polymers (SAP) that can absorb several times their weight of urine or other liquid.

The various parts of a disposable absorbent article are bonded together directly or indirectly. Hotmelt adhesives have been used to bond individual layers, in particular topsheet, backsheet and absorbent core which together form the chassis of the articles. Hotmelt adhesives have also been used to bond other discrete parts, such as fasteners and leg elastics or cuffs, to the chassis of the article. The hotmelt adhesives are often called construction adhesives for these applications because they help constructing the absorbent article from individual components. An adhesive is also used to form a backsheet laminate comprising a liquid impermeable film and an outwardly-facing nonwoven cover. Other bonding means such as fusion bonding and ultrasonic bonding are also used but these are typically not practical for thin layers and when large surface are to be bonded.

Hotmelt adhesives are made by combining polymers and additive components in a substantially uniform thermoplastic blend. Typical additive components include tackifiers, plasticizers, and/or waxes.

Various hotmelt compositions have been disclosed in the art. WO2019/204,541 (Turner et al.) discloses that adhesive compositions having a viscosity from about 2.000 mPa·s to about 11,500 mPa·s at 150° C., a Storage Modules (G') at 37° C. between about 3 MPa to about 9.5 MPa, a Yield Stress at 37° C. of from about 0.8 MPa to about 1.45 MPa perform well in adhesive stiff film laminates and typically also perform well in nonwoven-nonwoven laminates. These adhesive hotmelt compositions comprise a copolymer and preferably have a Toughness at 37° C. of from about 2 MJ/m³ to about 8 MJ/m³.

Instead of using formulated adhesives, unblended polymers have been proposed. An unblended polymer consists only of one type of polymer (generated via its own and specific polymerization process) rather than a blend of polymers which are made via separate polymerization process and mixed (blended) together after polymerization. Unblended polymers may additionally comprise minor amounts of additives such as antioxidants, perfumes and other low molecular weight components, but are substantially free of other polymers, mineral oils, or tackifiers.

Hotmelt compositions comprising metallocene-catalyzed propylene based copolymers have been proposed, see for example WO2016/153663A1, WO2014/194074A1, WO2019/94659A1 and US2020/0108168A1. US2016/053149A1 (Clamant) for example discloses a ready-to-use hotmelt adhesive comprising at least 95% of one or more polyolefin copolymer waxes, which have been prepared by means of metallocene catalysts, characterized in that the polyolefin copolymer wax consists of propylene and one or more further monomers selected from ethylene and branched or unbranched 1-alkenes having 4 to 20 C atoms and the content of structural units derived from propylene in the copolymer waxes amounts to 80 to 99.9% by weight, and the hotmelt adhesive has a surface tension of the melt, measured at a temperature of 170° C., of at most 23 mN/m.

Clamant manufactures and sells pure polyolefins manufactured by metallocene catalysts (mPO) under the Licocene® brand which are advertised as hotmelt adhesives. Hotmelt compositions comprised of pure mPO's however were found to have some limitations. First: NW-Film bonds made with pure mPO's as adhesive are weak. They readily fail via an adhesion break between adhesive and film. Second: the open time of Licocenes (like Licocene 2502) is comparably short, and for some applications this requires the additional implementation of a bonding roll on the process, which goes along with capital cost. Third: they typically cause accretion of the adhesive downstream of the slot nozzle for high speed slot applications after run-times of 1 to 3 minutes show ("blobbing").

When developing a blend based on mPO's, the benefits of the pure mPO should be impacted as little as possible while the above indicated limitations need to be overcome.

Conventionally, it was found beneficial to add a plasticizer in order to compensate for a too high hotmelt blend viscosity. Normally, mineral oils are added for this purpose. Mineral oils have several drawbacks such as being volatile (odor), diffusing into other substrate like PE films or onto the surfaces of other materials (like SAP) over time, which weakens the bond and deteriorates the function of other parts of the diaper. Mineral oils also contribute to lower thermal stability of the adhesive in the heated melting tank during processing causing faster thermal degradation of the adhesive over time.

There is thus a need for a hotmelt composition that can provide good nonwoven-film bonds, ideally also for nonwoven-nonwoven bonds, and which can be optionally formulated without mineral oil.

SUMMARY OF THE INVENTION

In a first aspect, the invention is for a hotmelt composition comprising:
- a low molecular weight metallocene-catalyzed polymer having a peak molecular weight below 130,000 g/mol;
- a high molecular weight polyolefin having a peak molecular weight of from 130,000 g/mol to 700,000 g/mol;
- an amorphous polyolefin having an enthalpy of crystallization of less than 10 J/g; and
- a tackifier.

The hotmelt compositions according to the invention may be formulated with relatively low amount, and preferably is free of, mineral oil. The hotmelt compositions may be used in particular in absorbent hygiene articles such as baby diapers, adult incontinence diapers, or sanitary napkins to make nonwoven-film bonds and/or nonwoven-nonwoven bonds. In a second aspect, the invention is thus for an absorbent article comprising a first and second substrate bonded to each other by the hotmelt composition. The invention is in a third aspect for a process for bonding a first substrate to a second substrate with the hotmelt composition.

The inventors have found that the high molecular weight polyolefins described herein exert a surprisingly strong strain hardening effect, i.e., an even increased resistance with crack progressing deformation. Strain hardening is believed to be a "self-repairing" mechanism of the hotmelt composition when being strained, which avoids early rupture. The hotmelt formulations of the invention can also be easily applied with a desirable open time.

The above-mentioned and other features and advantages of the present disclosure, and the manner of attaining them, will become more apparent and the disclosure itself will be better understood by reference to the following description.

DETAILED DESCRIPTION

Introduction

"Comprise," "comprising," and "comprises", as used herein, are open ended terms, each specifies the presence of what follows, e.g., a component, but does not preclude the presence of other features, e.g., elements, steps, components known in the art, or disclosed herein. Any features indicated below is optional unless indicated otherwise. Unless otherwise specified, each of the components of the invention may comprise one or more sub-components having the specified properties. For example, "a" low molecular weight polymer" means "one or more low molecular weight polymer(s)", having the specified molecular weight.

The components of the hotmelt compositions of the invention are described in further details below.

Low Molecular Weight Metallocene-Catalyzed Polymer

The hotmelt composition comprises a low molecular weight metallocene-catalyzed polymer having a peak molecular weight below 130,000 g/mol. The peak molecular weight may be for example in the range of from 5,000 g/mol to 130,000 g/mol. The peak molecular weight is measured as indicated further below in the experimental section. As for any of the components indicated in the claims, the composition may comprise one, or a blend of two or more, such low molecular weight metallocene-catalyzed polymers. Thus, unless indicated otherwise, when using the term "a low molecular weight metallocene-catalyzed polymer" it is meant the "one or more low molecular weight metallocene-catalyzed polymer(s)".

The hotmelt composition may typically comprise from 20% to 70% by weight of the low molecular weight metallocene-catalyzed polymer (or mixture thereof), in particular from 30% to 60% by weight of the low molecular weight metallocene catalyzed polymer(s).

Metallocene-catalyzed polymers typically have a regular spatial repeat monomer unit distribution and a narrow molecular weight distribution, as is known in the art. Metallocene-catalyzed polymers useful in the present invention can be described as low- or semi-crystalline with an enthalpy of crystallization, as measured according to the Enthalpy of Crystallization Test Method described below, typically ranging of from 5 J/g to 45 J/g.

The low molecular weight metallocene-catalyzed polymer may in particular be propylene-based. The propylene-based metallocene-catalyzed polymers may be homopolymers or copolymers, in particular propylene-ethylene copolymers.

The propylene-ethylene copolymers comprise at least 50% by weight of the copolymer of propylene unit, in particular at least 60%, or at least 70%, or at least 80% by weight. The remaining monomers are ethylene monomers, and optionally other alpha olefin monomers may be present in the co-polymers, for example 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof. The exact monomer distribution is typically published by the supplier, but can also be determined by a suitable method, such as nuclear magnetic resonance or infrared spectroscopies.

Suitable metallocene-catalyzed propylene-ethylene copolymers are commercially available from Clariant under the polymer range Licocene®, with a broad range of properties such as molecular weight, viscosity, crystallinity, etc. US2016/053149A1 assigned to Clariant also describes suitable co-polymers and on page 5 indicates that these examples were produced by the processes indicated in EP571,882. For a given catalyst system and given comonomer ratio, the molecular weight was regulated via the hydrogen partial pressure as molar mass regulator.

The low molecular weight metallocene-catalyzed polymer may further comprise a blend of two co-polymers, in particular:
  a first low molecular weight metallocene-catalyzed propylene-ethylene copolymer having an enthalpy of crystallization below 20 J/g; and
  a second low molecular weight metallocene-catalyzed propylene-ethylene copolymer having an enthalpy of crystallization above 20 J/g.

While not wishing to be bound by theory, it is believed that the stiffness of a hotmelt composition based on semi-crystalline polymers is linked to the crystallinity of the polymers. Therefore, the crystallinity of the low molecular weight metallocene based polymer, which is the backbone of the formula, should be considered when formulating a composition according to the invention. The enthalpy of crystallization is measured according to the Enthalpy of Crystallization Test Method described below.

The first low molecular weight metallocene-catalyzed propylene-ethylene copolymer has an enthalpy of crystallization of less than 20 J/g, in particular from 5 J/g to 15 J/g, and may be described as low-crystalline. A commercial example of the first copolymer is Licocene® PP 1602 from Clamant. Licocene PP 1602 is sold as granules and is described as a low melting, metallocene-technology based propylene-ethylene copolymer, which exhibits a low degree of crystallinity. The Mp of Licocene® PP 1602 was measured to be 75,900 g/mol and its enthalpy of crystallization of 16.7 J/g (see measurement method below). Another example is Licocene® PP 1302. The Mp of Licocene® PP 1302 was measured to be 24,100 g/mol and its enthalpy of crystallization of 11.8 J/g.

The second low molecular weight metallocene-catalyzed propylene-ethylene copolymer has a higher enthalpy of crystallization than the first copolymer, of at least 20 J/g, in particular from 25 J/g to 45 J/g. Polymers in this range can be described as semi-crystalline. The second copolymer may have a Mp in the range of from 50,000 g/mol to 130,000 g/mol, or from 60,000 g/mol to 110,000 g/mol. A commercial example of the second copolymer is Licocene® PP 3602 which is sold as granules and is described as a low crystalline metallocene-catalyzed propylene-ethylene copolymer. Licocene® 3602 has a measured enthalpy of crystallization of 35.0 J/g.

The first and second copolymers described above may be typically blended at a weight ratio of 10:90 to 90:10, for example 50:50 or 2:1 or 1:2. Blending two lower molecular weight copolymers with different crystallinity was found to enable low stiffness (as specifically required for NW-Film construction bonds), while still maintaining high toughness (as generally required for NW-NW and NW-Film construction bonds).

An example is a blend of Licocene® 3602 and Licocene® 1602, which are both propylene-ethylene copolymers from Clariant. Licocene 3602 is a relatively highly crystalline polymer while Licocene 1602 has a medium crystallinity. In a blend of both copolymers, the overall crystallinity can be adjusted in a way that the resulting hotmelt composition has a low enough Stiffness as required for strong NW-Film bonds but still a high Toughness. For example, a "building block" of Licocene 1602 and Licocene 3602 in a 2:1 ratio is believed to be superior to using pure Licocene 2502. The 2:1 blend of 1602 and 3602 has a lower crystallinity and hence lower Stiffness than Licocene 2502, while the higher peak molecular weights of 1602 and 3602 (75,900 and 62570 g/mol), compared to 2502 (57,100 g/mol), compensate on the Toughness. Of course, other ratios can be used depending on the application.

The low molecular weight metallocene-catalyzed polymer may also consist of a single low molecular weight metallocene-catalyzed polymer co-polymer. The inventors found the low molecular weight metallocene-catalyzed polyolefin Licocene® PP 2402 from Clamant particularly suitable for this purpose, because it enables the use of high molecular weight polyolefins with a peak molecular weight—particularly above 200,000 g/mol—while still keeping the viscosity low, e.g. below 3000 mPa·s at 150° C. A low viscosity is required whenever the hot adhesive is to be applied directly onto a heat sensitive substrate, like e.g. a polyethylene film as the "first substrate", rather than onto a less heat sensitive polypropylene non-woven which is later combined with the heat sensitive substrate (as the "second substrate"), after the adhesive has already cooled down to some extent. Licocene® PP 2402 from Clariant is a low molecular weight metallocene-catalyzed polyolefin, which has an enthalpy of Crystallization of about 24 J/g, a peak molecular weight (Mp) of about 28,000 g/mol and a viscosity at 150° C. of about 2,000 mPa·s.

High Molecular Weight Polyolefin

According to the invention, the inventors found that the cohesive strength of the formulation can be significantly increased when a polyolefin having a high peak molecular weight Mp of from 130,000 g/mol to 700,000 g/mol is used. The high molecular weight polyolefin may have a peak molecular weight which is at least greater by 10,000 g/mol than the peak molecular weight of the low molecular weight metallocene-catalyzed polymer(s) described above (taking the highest value for blends), in particular at least 20,000 g/mol, or even at least 50,000 g/mol greater. The high molecular weight polyolefin may in particular have a peak molecular weight of from 140,000 g/mol to 410,000 g/mol, or from 150,000 g/mol to 360,000 g/mol.

The inventors have surprisingly found that the addition of a longer molecular weight polyolefin significantly increases the strain hardening of the blend besides increasing the elongation at break, which in combination results in a significantly higher Toughness of the formulation. Strain hardening is believed to be a "self-repairing mechanism of the blend when being strained, which avoids early rupture.

The high molecular weight polyolefin may be advantageously comprised of a single material to simplify the compounding and formulation of the hotmelt composition, but it is not excluded that it may also be a blend of individual material falling under this definition. The hotmelt composition may typically comprise from 1% to 20% of such a high molecular weight polyolefin (or mixture thereof), by weight of the hotmelt composition, in particular from 2% to 15%, especially from 5% to 10% by weight of the hotmelt composition. It is believed that already small additions of the longer molecular weight polyolefins can significantly boost the strain hardening and hence the Toughness. More than 10% may on the other hand increase the viscosity. Toughness, strain hardening and Elongation at break are measured and observed in the Extensional Test Method, submitting the adhesive to large deformations, as relevant when the bond is subjected to forces in use.

The high molecular weight polyolefins may be a homopolymer or a copolymer. The copolymer may comprise different alpha olefin monomers such as ethylene, propylene, 4-methyl-1-pentene, pentene-1, 2-methylpentene-1, 3-methylbutene-1, heptene-1, dimethylpentene-1, trimethylbutene-1, ethylpentene-1, methylpentene-1, trimethylpentene-1, methylethylpentene-1, 1-octene, diethylbutene-1, propylpentane-1, decene-1, methylnonene-1, nonene-1, trimethylheptene-1, methylethylbutene-1, dodecene-1, and hexadodecene-1, and combinations thereof.

Nonlimiting examples of commercially available high molecular weight polyolefins are Affinity EG 8200G, Engage 8200, Infuse 9817, Vistamaxx 3000, Vistamaxx 6102, Vistamaxx 6202, Vistamaxx 6502, VERsify 4200, VERsify 4301.

The high molecular weight polyolefin may be in particular a propylene-ethylene copolymer. The high molecular weight polyolefin may in particular be a propylene-ethylene copolymer comprising greater than 80 wt. % of polypropylene units with isotactic stereochemistry. The high molecular weight polyolefin may also be a metallocene-catalyzed based copolymer, in particular a metallocene-catalyzed propylene-ethylene copolymer. Examples of such copolymers are commercially available as the Vistamaxx series from ExxonMobil. For example, Vistamaxx 6202 and Vistamaxx 6502 are sold as pellets and are described by their manufacturer as primarily composed of isotactic propylene repeat units with random ethylene distribution, produced using a metallocene catalyst technology. Vistamaxx 6202 and 6502 were used as high molecular weight polymer in the formula examples below. Vistamaxx 6502 has the lowest viscosity, and thus the least impact on increasing the viscosity of the total composition.

A higher molecular weight was found advantageous to enable the required Toughness, as long as it can still be balanced versus the increase of viscosity. Particularly for applications where sprayable adhesives at or below 155° C. are required to avoid thermal damage of heat sensitive first substrates, there are normally limitations in the choice of the high molecular weight polyolefin to avoid too high viscosities. Normally polyolefins with a melt flow rate of 20 g to 300 g/10 min measured at 230° C./2.16 kg in accordance with ASTM D1238 are used, for example Vistamaxx 6502, whereas higher molecular weight polyolefins with accordingly low melt flow rates, specifically a melt flow rates of below 20 g/10 min measured at 230° C./2.16 kg, such as Vistamaxx 6202, are normally avoided to keep the viscosity of the composition low.

The present invention also enables the use of higher molecular weight polyolefins with a melt flow rate below 20 g/10 min measured at 230° C./2.16 kg, while still enabling a low viscosity and good sprayability for the composition. This is enabled by the combination with low molecular weight polyolefins with a Heat of Crystallization in the range of 20 J/g to 30 J/g and a peak molecular weight between 25,000 and 35,000 g/mol, such as Licocene PP 2402.

Amorphous Polyolefin

According to the invention, it was fund that adding an amorphous polyolefin to the polymers described above provides a hotmelt adhesive which is processable. The hotmelt composition may comprise a single amorphous polyolefin or a mixture thereof. In the following, "amorphous polyolefin" means "at least one amorphous polyolefin(s)", unless specified otherwise. The hotmelt adhesive composition may comprise at least 1% by weight of such amorphous polyolefin, in particular the amorphous polyolefin may range from 1% to 30%, in particular from 2% to 25%, or from 5% to 25%, by weight of the hotmelt adhesive composition.

The amorphous polyolefin preferably has an enthalpy of crystallization, measured in accordance with Enthalpy of Crystallization Test Method described below, of less than 10 J/g, preferably of less than 5 J/g, more preferably less than 1 J/g. The amorphous polyolefin preferably has no crystallinity and thus has an enthalpy of crystallization of (about) 0 J/g. The amorphous polyolefin may also be a propylene-based polymer.

The amorphous polyolefin may have one or more, or all, of the following properties:
- a pour point of <50° C., preferably <30° C., more preferably <25° C.;
- a viscosity at 170° C. between 20 and 3000 mPa·s, preferably from 50 to 1000 mPa·s, particularly preferably from 80 to 500 mPa·s (see Viscosity Test Method below);
- a density at 23° C. of less than 0.95 g/cm$^3$, preferably of less than 0.92 g/cm$^3$, in particular between 0.83 g/cm$^3$ and 0.90 g/cm$^3$ (as measured according to ISO 1183);
- a glass transition temperature of <−35° C., preferably <−40° C., more preferably <−45° C., as determined by the DSC method according to DIN 11357-2;
- a polydispersity index of less than 5, preferably less than 3, particularly preferably less than 2.5. The polydispersity index PDI is calculated from the quotient of weight-average molecular weight Mw and number-average molecular weight Mn and is determined according to the standard ISO 16014.

The amorphous polyolefin supports the function of the base polymers. This results in further advantages for the user. For example, fewer components need to be melted and mixed, resulting in faster and more cost-effective working processes. The hotmelt compositions of the present invention may be advantageously be free of wax or nucleation agent. The hotmelt compositions of the present invention may also be advantageously be free of plasticizer.

The amorphous polyolefin of the invention preferably comprises or consists of at least one propylene-based polymer. The propylene-based polymer may be linear propylene homopolymers or copolymers produced using Ziegler or metallocene catalysts which have a propylene content of at least 50% by weight or more. Suitable monomers materials preferably comprise propylene and one or more other monomers selected from the group consisting of ethylene and higher α-olefins of C4-C18. The amorphous polyolefin may in particular be a propylene-ethylene copolymer.

The amorphous propylene-based polymer is preferably produced by metallocene catalysis and is preferably an amorphous poly alpha olefine copolymer. Without wishing to be bound by theory, the inventors believe that a metallocene catalyzed propylene-based amorphous polymer enables better compatibility with the other metallocene catalyzed propylene-based polymers in the composition. The amorphous propylene-based polymer may be a copolymer of propylene and another monomer selected from the group consisting of ethylene and C4-C18 α-olefins. The amorphous propylene-based polymer may have a glass transition temperature Tg, determined by DSC in accordance with DIN EN ISO 11357-2, of less than −20° C., preferably less than −30° C. and particularly preferably less than −40° C.

The amorphous propylene-based polymer may be a random copolymer of propylene with a propylene proportion of less than 90% by weight, preferably with a propylene proportion between 60-85% by weight, more preferably between 72-82%. The amorphous propylene-based polymers may be a copolymer of propylene and ethylene, wherein said copolymer is derived from 60-85% by weight propylene and from 15-40% by weight ethylene.

The amorphous polyolefin has advantageously a weight average molecular weight measured according to DIN 55672 between 1,000 g/mol and 50,000 g/mol, preferably between 5,000 g/mol and 30,000 g/mol. In particular, the amorphous polyolefin used may be a low molecular weight polymer with a weight-average molecular weight Mw of less than 10,000 g/mol, preferably less than 9,000 g/mol, particularly preferably less than 7,000 g/mol (measured according to DIN 55672).

The amorphous polyolefin has advantageously a viscosity at 170° C. below 500 mPa·s, most preferably below 300 mPa·s. The amorphous polyolefin has advantageously a viscosity at 190° C. below 500 mPa·s, preferably from 10 mPa·s to 300 mPa·s, more preferably from 50 mPa·s to 200 mPa·s. The low viscosity of the amorphous polyolefin enables a formulation which is essentially free of mineral oils, still having sufficiently low viscosities of the resulting blends to enable processing via slot and spray applications.

The amorphous polyolefin exemplified herein, Licocene PPA 330 from Clariant, is a metallocene-catalyzed propylene-based copolymer having a weight-average molecular weight Mw of less than 10,000 g/mol (however other amorphous polyolefins are also suitable). As it is completely amorphous (both the crystallization enthalpy and melting enthalpy, as measured via DSC, are zero) no melting point can be detected in DSC. Licocene PPA 330 has the following properties:

a propylene content of 79.5% by weight;

a pour point of 21° C.;

a viscosity at 170° C. of 141 mPa·s and at 190° C. of 93 mPa·s;

a glass transition temperature of −44° C., as determined by the DSC method according to DIN 11357-2;

a polydispersity index of 1.5 (according to the standard ISO 16014).

Tackifier

The hotmelt composition comprises a tackifier (one or a mixture of tackifiers). It was found that the tackifier can increase the cohesive strength and the open time of the composition. The hotmelt composition can typically comprise from 10% to 70%, in particular from 20% to 65%, or from 25% to 60%, or 26% to 60%, or 30% to 60% by weight of the composition, of the tackifier(s). Tackifiers otherwise called "tackifier resins" or "tackifying resins" are low-molecular weight compounds (oligomers) that are added to adhesive formulations to improve tack and peel adhesion materials. Usual tackifiers known in the art may be used in the present invention. Typical tackifiers are thermoplastic materials stable at least up to 200° C., being amorphous glasses at room temperature, and having a Tg higher than 50° C., preferably comprised between 80° C. and 125° C. Tackifiers typically have a molecular weight comprised between 500 and 2000 g/mol.

Tackifiers are in general organic chemicals with polycyclic structure. Commonly used tackifiers are selected from rosin resins and their derivatives (rosin esters), hydrocarbon resins produced from petroleum-based by-products of naphtha crackers, and terpene resins (modified or not). Hydrocarbon resins may be aliphatic, cycloaliphatic and aromatic resins (in particular C5 aliphatic resins, C9 aromatic resins, and C5/C9 aliphatic/aromatic resins), and may be optionally hydrogenated hydrocarbon resins.

Exemplary tackifiers include aliphatic hydrocarbon resins, aromatic modified aliphatic hydrocarbon resins, hydrogenated poly-cyclopentadiene resins, poly-cyclopentadiene resins, gum rosins, gum rosin esters, wood rosins, wood rosin esters, tall oil rosins, tall oil rosin esters, poly-terpenes, aromatic modified poly-terpenes, terpene-phenolics, aromatic modified hydrogenated poly-cyclopentadiene resins, hydrogenated aliphatic resins, hydrogenated aliphatic aromatic resins, hydrogenated terpenes and modified terpenes, and hydrogenated rosin esters. Particularly suitable tackifiers are rosin (and its derivatives) resins and hydrogenated hydrocarbon tackifiers, which are solid at room temperature. The tackifier is preferably at least partially hydrogenated, preferably fully hydrogenated. Without wishing to be bound by theory, the inventors believe that a partially or particularly fully hydrogenated tackifier enables better compatibility with the other components of the adhesive composition of the present invention. Also, a fully hydrogenated tackifier is preferred due its lower tendency to deteriorate the odor of the adhesive formulation and hence the absorbent article.

Compounding and Optional Ingredients

The hotmelt composition can be prepared by heating the polymers at a sufficiently elevated temperatures (e.g., about 135° C. to about 175° C.) to melt the polymers. The tackifier and other ingredients (e.g., additive or other polymers) can be added to this molten primary polymer blend. A mixer can be used to mix the polymers and other additives together into a final hotmelt composition.

The resulting blend is cooled and conditioned for transport and storage. During application, the hotmelt composition is molten again and can be applied to a substrate using any known applicator devices, in particular slot coating which is a contact applicator.

The hotmelt composition according to the invention preferably has a viscosity at 170° C. is in the range from about 1,000 mPa·s to about 7,000 mPa·s, as measured according to the Viscosity Test Method as described herein.

There are significant advantages to minimizing or avoiding the use of a mineral oil. This can reduce the cost of the hotmelt composition, as well as eliminate an additional ingredient and potential issues that may be associated with supplying the additional ingredient.

The hotmelt composition may optionally comprise an antioxidant. Non-limiting examples of suitable antioxidants include amine-based antioxidants such as alkyl diphenyl amines, phenyl-naphthylamine, alkyl or aralkyl substituted phenyl-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetrakis [(methylene(3,5-di-t-butyl-4-hydroxyhydrocinnamate)]methane (e.g., IRGANOX™ 1010, from Ciba Geigy, New York); octadecyl-3,5-di-t-butyl-4-hydroxycinnamate (e.g., IRGANOX™ 1076, commercially available from Ciba Geigy) and combinations thereof. When used, the amount of the antioxidant in the hotmelt composition can be respectively less than 1%, alternatively from about 0.05% to about 0.75%, and alternatively from about 0.1% to about 0.5%, by weight of the hotmelt composition.

The hotmelt composition may optionally comprise a UV stabilizer that may prevent or reduce the degradation of the composition by radiation. Any UV stabilizer known to a person of ordinary skill in the art may be used in the hotmelt composition. Non-limiting examples of suitable UV stabilizers include benzophenones, benzotriazoles, aryl esters, oxanilides, acrylic esters, formamidine carbon black, hindered amines, nickel quenchers, hindered amines, phenolic antioxidants, metallic salts, zinc compounds, and combinations thereof. Where used, the amount of the UV stabilizer in the hotmelt composition can be less than 1%, alternatively from about 0.05% to about 0.75%, and alternatively from about 0.1% to about 0.5%, by weight of the hotmelt composition.

The hotmelt composition may optionally comprise a brightener, colorant, and/or pigment. Any colorant or pigment known to a person of ordinary skill in the art may be used in the hotmelt composition. Non-limiting examples of suitable brighteners, colorants, and/or pigments include fluorescent materials and pigments such as triazine-stilbene, coumarin, imidazole, diazole, titanium dioxide and carbon black, phthalocyanine pigments, and other organic pigments such as IRGAZINB, CROMOPHTALB, MONASTRALB, CINQUASIAB, IRGALITEB, ORASOLB, all of which are available from Ciba Specialty Chemicals, Tarrytown, N.Y. Where used, the amount of the brightener, colorant, and/or pigment in the hotmelt composition can be less than 10%, alternatively from about 0.01% to about 5%, and alternatively from about 0.1% to about 2%, by weight of the hotmelt composition.

The hotmelt composition may optionally comprise a fragrance such as a perfume or other odorant. Such fragrances may be retained by a liner or contained in release agents such as microcapsules that may, for example, release fragrance upon removal of a release liner from or compression on the adhesive composition. Where used, the amount of the fragrance in the hotmelt composition can be less than 3%, alternatively less than 2%, alternatively less than 1%, alternatively from about 0.05% to about 0.75%, and alternatively from about 0.1% to about 0.5%, by weight of the hotmelt composition.

Hotmelt Composition Properties

The hotmelt composition according to the invention may have a least one, and preferably all, of the following properties:

- a viscosity at 150° C. is in the range from about 2,000 mPa·s to about 15,000 mPa·s, as measured according to the Viscosity Test Method as described herein;
- a storage modulus (G') at 37° C. smaller than 9.5 MPa, preferably smaller than 7.5 MPa, most preferably below 5 MPa, as measured in the cold to hot temperature ramp by the Oscillatory Rheometry Test Method disclosed herein;
- a Yield Stress at 37° C. smaller than 1.7 MPa, as measured by Extensional Test Method disclosed herein;
- a Toughness above 2 MJ/m$^3$, preferably above 5 MJ/m$^3$, as measured by the Extensional Test Method disclosed herein;
- a Cross Over temperature below 70° C., preferably below 65° C., as measured in the hot to cold temperature ramp according to the Oscillatory Rheometry Test Method disclosed herein.

Renewable Materials

Any of the ingredients of the hotmelt composition may be partially obtained from renewable sources, in particular any of the component or the hotmelt composition as a whole may have a bio-based content of at least 50%. "Bio-based content" refers to the amount of carbon from a renewable resource in a material as a percent of the mass of the total organic carbon in the material, as determined by ASTM D6866-10, method B.

The metallocene catalyzed polyolefins used in the present invention can be used with significant (at least 50%) bio-based content. The Licocene grades from Clariant can be used in the renewable-based version under the trade-name Terra. So, instead of the grade "Licocene PPA 330" the grade "Licocene PPA 330 Terra" can be used, or instead of the grade "Licocene PP 1602" the grade "Licocene PP 1602 Terra" can be used.

EXAMPLES & DATA

Table 1 discloses the peak molecular weight (Mp) in g/mol of some commercially available polymers that may be used in the invention.

TABLE 1

| | Mp |
|---|---|
| Licocene PPA 330 | 12,395 |
| Licocene PP 1302 | 24,100 |
| Licocene PP 1602 | 75,900 |
| Licocene PP 2402 | 28,470 |
| Licocene PP 2502 | 57,100 |
| Licocene PP 3602 | 62,570 |
| Vistamaxx 3000 | 299,500 |
| Vistamaxx 6102 | 687,700 [1] |
| Vistamaxx 6202 | 214,100 |
| Vistamaxx 6502 | 185,300 |

[1] correlated (not measured directly)

Table 2 discloses the enthalpy of crystallization in J/g of some commercially available polymers that may be used in the invention:

TABLE 2

| | Enthalpy of Crystallization (J/g) |
|---|---|
| Licocene PP 1302 | 11.8 |
| Licocene PP 1602 | 16.7 |
| Licocene PP 2502 | 29.4 |
| Licocene PP 3602 | 35.0 |
| Licocene PPA 330 | 0 |

Table 3 shows exemplary formulations according to the invention (all ingredient values indicated in weight percent). The open time of each exemplary composition can be assessed using the Cross Over Temperature [° C.] method, from hot to cold, which measures the temperature at which the hotmelt composition solidifies when cooling down. A lower Cross Over Temperature correlates with a longer open time for the hotmelt adhesive because, for a given application temperature (typically 160° C.), it takes a longer time for the adhesive at a given basis weight to cool down to reach the Cross Over Temperature. The hotmelt compositions of the present invention excel by a long open time, which was found advantageous for the adhesive bonds in the diaper for which the composition is preferably used. Those bonds are primarily NW-Film bonds in chassis applications that require typically complex making processes on production lines, which go along with longer distances between the adhesive application onto the first substrate and the combining with the second substrates or additional cooling via vacuum (e.g. to temporarily fixate cut pieces of substrates with adhesive before they are attached onto a second substrate). The inventors found that propylene rich formulations and the absence of waxes or nucleation agents contribute to enable the required long open time of the formulation. The inventors found that the Cross Over temperature should be below 70° C., or preferably below 65° C. Also shown are the Toughness, the Storage modulus (G') and the Yield Stress, with the latter two being measures of the stiffness of the hotmelt composition.

TABLE 3

| | Ex. 1 | Ex. 2 | Ex. 3 | Ex. 4 | Ex. 5 | Ex. 6 | Ex. 7 | Comparative Example Licocene 2502 | Comparative Example DM3166 |
|---|---|---|---|---|---|---|---|---|---|
| Licocene PP 1602/3602 (2:1) | 40% | 30% | 38% | 35.5% | 38% | — | — | | |

TABLE 3-continued

|  | Ex. 1 | Ex. 2 | Ex. 3 | Ex. 4 | Ex. 5 | Ex. 6 | Ex. 7 | Comparative Example Licocene 2502 | Comparative Example DM3166 |
|---|---|---|---|---|---|---|---|---|---|
| Licocene PP 2402 | — | — | — | — | — | 35.5% | 38.0% | | |
| Eastotac H-100L | 40.0% | 40.0% | 40.0% | 40.0% | — | — | — | | |
| Henghe HM1000 | — | — | — | — | 40.0% | 40.0% | 40.0% | | |
| Vistamaxx 6502 | 10.0% | 10.0% | 5.0% | 7.5% | — | 7.5% | — | | |
| Vistamaxx 6202 | — | — | — | — | 5.0% | — | 5.0% | | |
| Licocene PPA 330 | 10.0% | 20.0% | 17.0% | 17.0% | 17.0% | 17.0% | 17.0% | | |
| Highest Cross Over Temperature [° C.] | 52 | 56 | 60 | 63 | 34 | 42 | 47 | 73 | 82 |
| G' at 37° C. [MPa] | 1.6 | 1.6 | 1.7 | 2.3 | 1.0 | 1.0 | 0.9 | 33.5 | 0.3 |
| Yield Stress at 37° C. [MPa] | 1.5 | 0.8 | 1.0 | 1.2 | 1.1 | 1.3 | 1.5 | 8.8 | 0.1 |
| Toughness at 37° C. [MJ/m$^3$] | 10.8 | 7.4 | 5.5 | 7.5 | 10.3 | 6.8 | 7.3 | 8.9 | 2.8 |
| Viscosity [mPa · s] at 150° C. | 14,000 | NA | NA | 6,900 | 5,400 | 2,700 | 2,500 | 3,200 | 4,900 |

Application Examples

In the below examples, the adhesives were slot coated with 1 mm wide stripes/1 mm gap between the stripes at a specified basis weight (on the stripes) onto a first substrate and combined with a second substrate. As only half of the area was covered, the average basis weight over the whole area is half of the basis weight on the stripes. The repeat pattern of stripes was applied over a Cross Direction dimension of 120 mm.

The peel strength of the laminates was measured with a tensile tester in the 180° peel mode at a crosshead speed of 305 mm/min. The peel strength is the average force per unit width required to separate the two bonded substrates where the angle of separation is 180 degrees. The force is averaged over the travel length while the sample is under tension. The samples were equilibrated at 23° C. and 50% relative humidity for at least 1 hour before testing at that same temperature. The specimens tested were in substantially rectilinear shape with a width of 1 inch (25.4 mm). The specimen's long axis is Cross Direction and includes the repeat pattern of adhesive stripes and the specimen's short axis with said width of 25.4 mm is Machine Direction. The axis of pull is the long axis of specimen, which corresponds to Cross Direction of the laminate. The test was stopped after 90 mm of travel length with the sample still under tension (not yet completely separated). The data were automatically collected by the TestWorks software purchased from MTS Systems Corporation, Eden Prairie, Minnesota. The force and extension data were acquired with a rate of 200 Hz during the test.

In the examples in table 4, the first substrate was a spunbonded nonwoven with a basis weight of 22 gsm and the second substrate was a polyethylene film with a basis weight of 15 gsm.

TABLE 4

| Adhesive | Adhesive Average Basis Weight [g/m$^2$] | Peel Strength [N/inch] |
|---|---|---|
| D3166 (comparative) | 1.0 | 0.15 |
| Ex. 4 (inventive) | 1.0 | 1.51 |
| Ex. 4 (inventive) | 0.5 | 1.46 |
| Ex. 4 (inventive) | 0.25 | 0.30 |
| Ex. 5 (inventive) | 1.0 | 1.05 |
| Ex. 5 (inventive) | 0.5 | 0.47 |
| Ex. 6 (inventive) | 1.0 | 0.27 |
| Ex. 7 (inventive) | 1.0 | 0.30 |
| Ex. 7 (inventive) | 0.5 | 0.24 |

Due to their lower viscosity, Ex. 6 and Ex. 7 can be also directly applied onto more heat sensitive substrates like polyethylene films, particularly via intermittent spray applications (like Summit®). In intermittent spray applications, larger droplets of the adhesive, which may form on the onset of the intermittent spray interval, can thermally damage the film, if the adhesive is applied at a too high temperature. So, Ex. 6 and 7 can be used for a larger variety of construction bonds, which enables to combine several adhesive applications into one and reduce the number of adhesive tanks at the diaper production lines. This additional benefit compensates for the relatively not as strong performance increase versus the reference in comparison to Ex. 4 and Ex. 5. Still, Ex. 6 and Ex. 7 enable a performance increase by a factor of about 2, which can be translated into an adhesive usage reduction by about a factor of 2.

In the examples of Table 5, the first substrate was a Landing Zone Laminate 44 and the second substrate a 22 gsm spunbonded nonwoven. The Landing Zone Laminate (EBLV, as available from 3M) consists of an extruded film layer (extrudate) and carded staple fibers, which have been thermally bonded to the extrudate. The total basis weight of the Landing Zone was 47.0 gsm, the fiber basis weight 22.0 gsm and the extrudate basis weight was 25.0 gsm. The adhesive was applied onto the film side of the Landing Zone with an adhesive average basis weight of 10.6 gsm. Because of the higher bond strength requirement of this bond in the diaper, a higher basis weight of the adhesive was used in these examples. These samples have been stored for 8 months at 23° C. before measurement. Without wishing to be bound by theory, the inventors believe that the absence of a mineral oil in the inventive formulation reduces the degradation of the bond over time which is typically observed with hot melt adhesives in nonwoven-film bonds due to diffusion of the mineral oil from the adhesive into the adjacent film.

TABLE 5

| Adhesive | Peel Strength [N/inch] |
|---|---|
| D3166 (comparative) | 3.51 |
| Ex. 4 (inventive) | 14.04 |
| Ex. 5 (inventive) | 13.12 |

General Description of an Absorbent Article

"Absorbent article", as used herein, refers to personal hygiene products that are placed against or in proximity to the body of the wearer to absorb and contain the various exudates discharged from the body. Absorbent articles include baby diapers, training pants, adult incontinence undergarments, feminine hygiene products, and the like. As used herein, the term "body fluids" or "body exudates" includes, but is not limited to, urine, blood, vaginal discharges and fecal matter.

Figure 1:
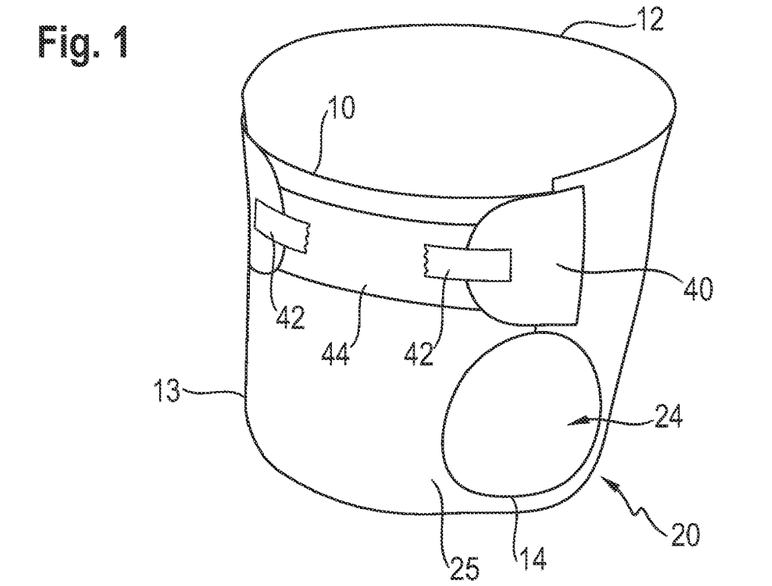
FIG. 1 shows a perspective view of an exemplary taped diaper in a closed configuration as it would be when worn by a wearer.
Figure 2:
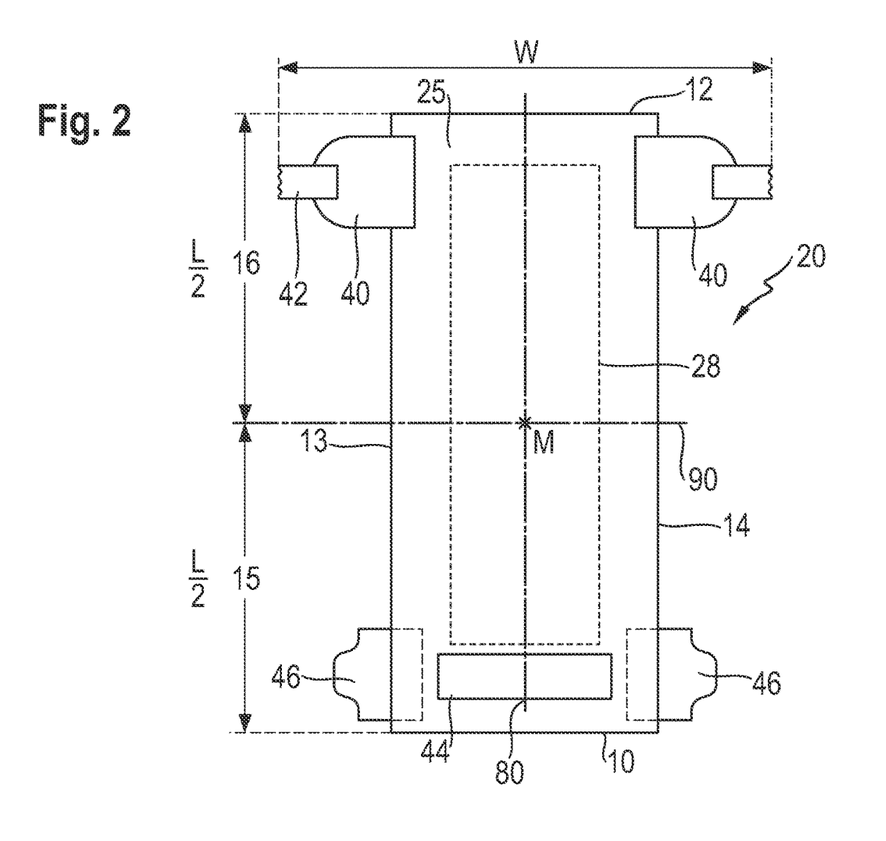
FIG. 2 shows the garment-facing side of the diaper of FIG. 1 with the diaper flattened out.
Figure 3:
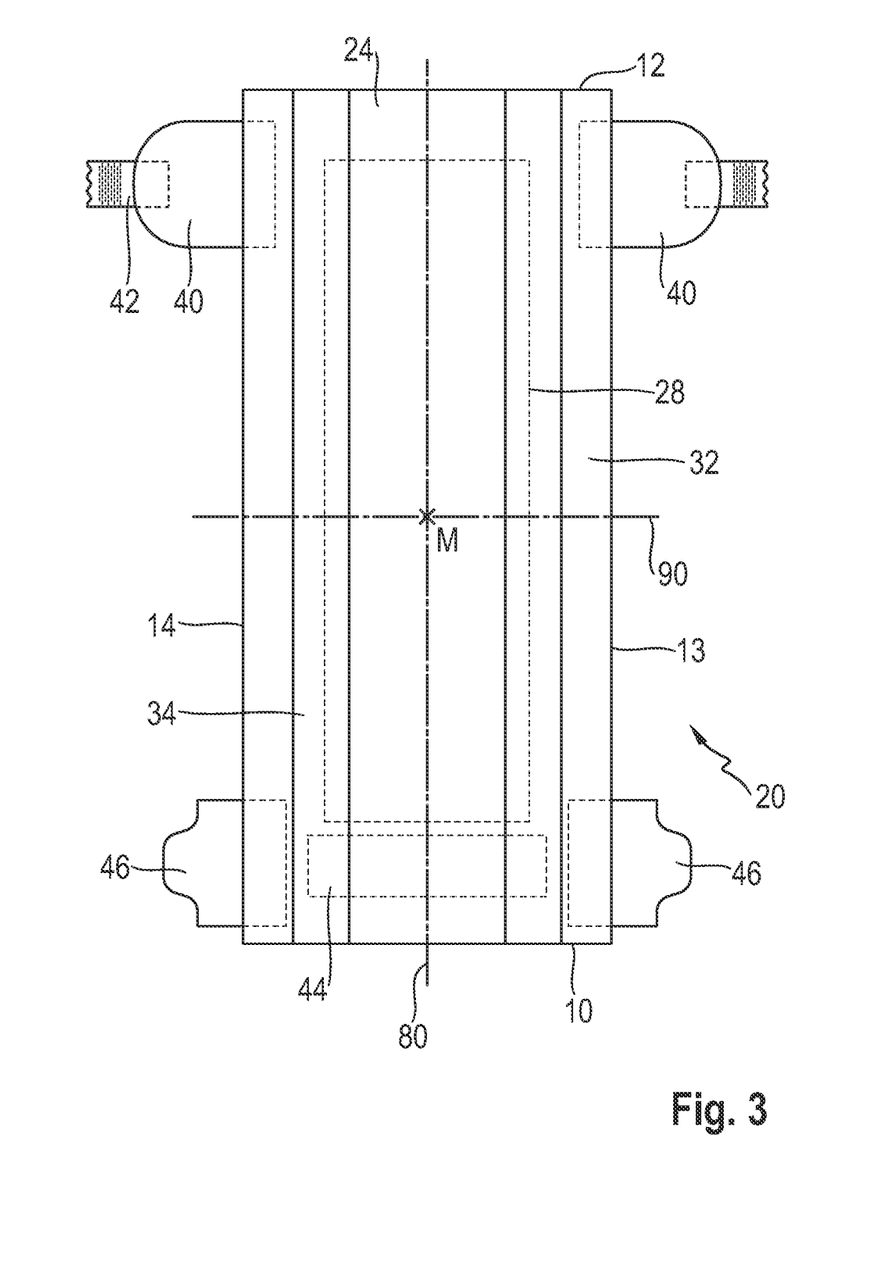
FIG. 3 shows the wearer-facing side of the diaper of FIG. 1 with the diaper flattened out.

An exemplary absorbent article according to the invention in the form of a baby taped diaper 20 is represented in FIGS. 1-3. FIG. 1 is a perspective view of the exemplary diaper in a closed state as it would appear when worn by a wearer. This taped diaper 20 is shown for illustration purpose only as the invention may be used for making a wide variety of diapers or other absorbent articles such as baby diaper pants, adult incontinence pants or feminine sanitary pads. In the following, the word "diaper" and "absorbent article" are used interchangeably. The Figures are used herein as illustration of one way to carry out the invention and are not limiting the scope of the claims, unless specifically indicated to do so.

The absorbent article comprises a liquid permeable topsheet 24 on its wearer-facing surface, a liquid impermeable backsheet 25 on its garment-facing surface and an absorbent core 28 between the topsheet and the backsheet (shown in dotted line in FIGS. 2 and 3). The topsheet typically forms the majority of the wearer-contacting surface of the article and is the first layer that the body exudates contact. The topsheet is liquid permeable, permitting liquids to readily penetrate through its thickness. Any known topsheet may be used in the present invention. The backsheet typically comprises a fluid impermeable plastic film, which may be printed with a backsheet pattern, and a low basis weight nonwoven outer cover glued to this impermeable film to give a nicer feel and appearance to the backsheet.

"Nonwoven", as used herein, is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to greater than 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm of g/m$^2$). Typical nonwovens that may be used in absorbent articles have a basis weight in the range of about 5 gsm to about 50 gsm, or up to about 40 gsm for example.

The absorbent article may also typically comprise a fluid acquisition layer and/or a fluid distribution layer between the topsheet and the absorbent core, which is not represented in the Figures for simplicity but are present in most diapers, as well as outer barrier cuffs 32 and inner barrier cuffs 34, as is known in the art. The absorbent article may also comprise other usual components if it is desired to increase the performance of the article, such as transverse barrier cuffs, front and/or back elastic waistbands, a lotion application on the topsheet, longitudinally extending channels in the core and/or the distribution layer, a wetness indicator, etc. . . . all these components have been extensively described and exemplified in the art. More detailed disclosures of example of such components are for example disclosed in WO201493323, WO2015/183669 (both Bianchi et al), WO 2015/031225 (Roe et al.) or WO2016/133712 (Ehrnsperger et al.) to name a few.

The absorbent article typically comprises a front edge 10, a back edge 12, and two longitudinally-extending side (lateral) edges 13, 14. The front edge 10 is the edge of the article which is intended to be placed towards the front of the user when worn, and the back edge 12 is the opposite edge, and together form the waist opening of the diaper. The lateral edges 13, 14 respectively form the two leg openings. The topsheet 24, the backsheet 25, the absorbent core 28 and the other article components may be assembled in a variety of well-known configurations, in particular by gluing, fusion and/or pressure bonding. The absorbent articles of the invention may comprise any typical layers and components used in absorbent products of the diaper type, and which are not necessarily represented in the simplified FIGS. 1-3. A plurality of absorbent articles may be packaged together in a package.

General Description of an Absorbent Core 28

"Absorbent core" means an absorbent structure disposed between topsheet and backsheet for absorbing and containing liquid such as urine received by the absorbent article. The absorbent core comprises an absorbent material, that is typically enclosed within or sandwiched between a core wrap. The core wrap may be a single material that is folded and attached to itself, or it may comprise a separate top layer and bottom layer that are bonded together. The absorbent material typically comprises superabsorbent particles which are optionally mixed with cellulose fibers. As used herein, "absorbent core" does not include any acquisition-distribution systems, topsheet, or backsheet of the absorbent article.

Figure 4:
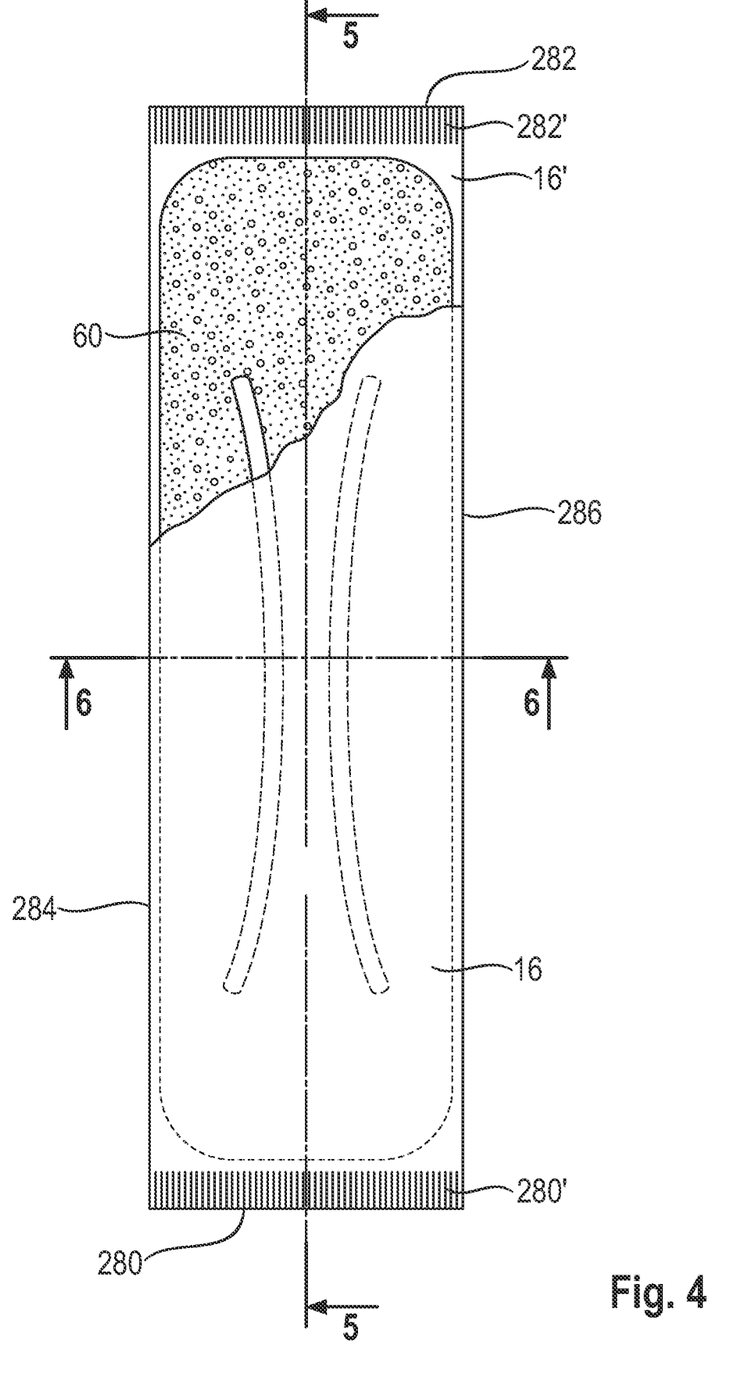
FIG. 4 shows a top view of an exemplary absorbent core with the top layer partially removed.

The absorbent core 28 is the component of the absorbent article having the most absorbent capacity. An exemplary absorbent core 28 is shown in isolation in FIGS. 4-6, in dry state (before use). The absorbent core may typically have a generally rectangular shape as defined by the longitudinal edges 284, 286 and transversal front edge 280 and back edge 282. The absorbent core 28 comprises an absorbent material 60, deposited as a layer having a generally rectangular outline, as represented on FIG. 4. This absorbent core represented is of course not limiting the scope of the invention as the invention is applicable to a wide variety of absorbent cores. It is also common to have an absorbent material 60 layer having a non-rectangular outline ("shaped" core), in particular the absorbent material layer may define a tapering along its width towards the central region of the core (or "dog-bone" shape). In this way, the absorbent material deposition area may have a relatively narrow width in an area of the core intended to be placed in the crotch region of the absorbent article. This may provide for example better wearing comfort. Other shapes can also be used such as a "T" or "Y" or "sand-hour" for the area of the absorbent material.

The absorbent material 60 may be any conventional absorbent material known in the art. For example, the absorbent material may comprise a blend of cellulose fibers and superabsorbent particles ("SAP"), typically with the percentage of SAP ranging from about 50% to about 75% by weight of the absorbent material. The absorbent material may also be free of cellulose fibers, as is known in so-called airfelt-free cores where the absorbent material consists of SAP.

"Superabsorbent polymer" or "SAP" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of at least 20 g/g, in particular of from 20 g/g to 40 g/g. "Superabsorbent polymer particles", as used herein, refers to a superabsorbent polymer material which is in particulate form so as to be flowable in the dry state.

Various absorbent core designs comprising high amount of SAP have been proposed in the past, see for example in U.S. Pat. No. 5,599,335 (Goldman), EP1,447,066 (Busam), WO95/11652 (Tanzer), US2008/0312622A1 (Hundorf), WO2012/052172 (Van Malderen). In particular the SAP printing technology as disclosed in US2006/024433 (Blessing), US2008/0312617 and US2010/0051166A1 (both to Hundorf et al.) may be used. The invention is however not limited to a particular type of absorbent core. The absorbent core may also comprise one or more glue such as an auxiliary glue applied between the internal surface of one (or both) of the core wrap layers and the absorbent material to reduce leakage of SAP outside the core wrap. A microfibrous adhesive net may also be used in air-felt free cores as described in the above Hundorf references. These glues are not represented in the Figures for simplicity.

The absorbent material may be deposited as a continuous layer within the core wrap. The absorbent material may also be present discontinuously for example as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern wherein the resulting layer is substantially continuously distributed across the absorbent particulate polymer material area. As for example taught in US2008/312622A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

Figure 5:
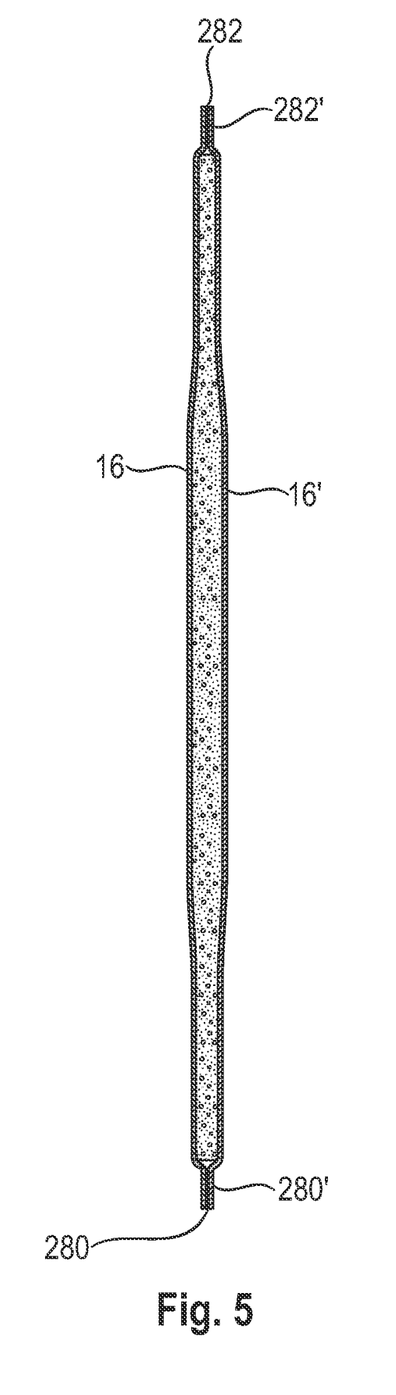
FIG. 5 shows a longitudinal cross-section view of the absorbent core of FIG. 4.
Figure 6:
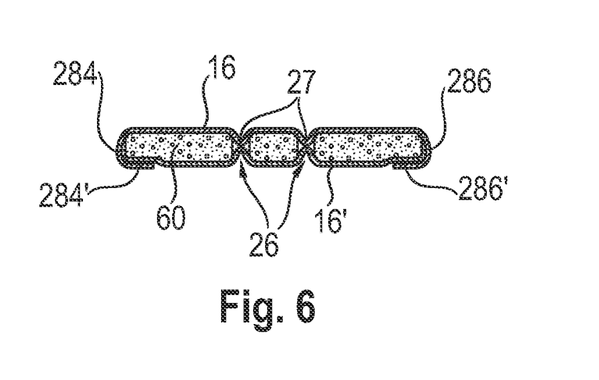
FIG. 6 shows transversal cross-section view of the absorbent core of FIG. 4.

The basis weight (amount deposited per unit of surface) of the absorbent material may also be varied to create a profiled distribution of absorbent material, in particular in the longitudinal direction (as schematically illustrated in FIG. 5) to provide more absorbency towards the center and the middle of the core, but also in the transversal direction, or both directions of the core. The absorbent core may also comprise longitudinally extending channels which are substantially free of absorbent material within the absorbent material area. The core wrap may be bonded through these material-free areas. Exemplary disclosures of such channels in an airfelt-free core can be found in WO2012/170778 (Rosati et al.) and US2012/0312491 (Jackels). Channels may of course also be formed in absorbent cores comprising cellulose fibers.

Core Wrap

The function of the core wrap is to contain the absorbent material. Different core wrap constructions can be used. A typical core wrap construction comprises two nonwoven substrates 16, 16', which are attached to another and form respectively the top layer 16 and the bottom layer of the core wrap 16'. These two layers may be typically attached to another along at least part of the periphery of the absorbent core to form a seal. Typically, neither the first nor the second substrate needs to be shaped, so that they can be rectangularly cut for ease of production, but other shapes are not excluded. The terms "seal" is to be understood in a broad sense. The seal does not need to be continuous along the whole periphery of the core wrap but may be discontinuous along part or the whole of it, such as formed by a series of seal points spaced on a line. Typically, a seal may be formed by gluing and/or thermal bonding.

The core wrap represented in the Figures comprises a top layer 16 which is wider than the bottom layer 16' so that two flaps of the top layer can be folded over the bottom layer along the longitudinal edges 284, 286 of the core respectively to which they are attached, typically by an adhesive to form the longitudinal seals 284', 286'. The front edge 280 and back edge 282 may also be sealed, for example by a sandwich seal 280', 282'. Such transversal seals may for example made by adhesive stripes applied in machine direction by the slot glue technique, as is known in the art. Alternatively, is it possible to leave the transversal edges 280, 282 open without a seal. For example, there may be enough core wrap material between the edges of the core and the absorbent material 60 to provide a buffer zone at these ends.

The invention is applicable to any of these core wrap seals as well as the core channel bonds 27 that will be discussed further below Alternatively, the core wrap may be made of a single piece of nonwoven which has been folded over itself around the absorbent material layer 60, and is bonded to itself along a single longitudinal seal, instead of two longitudinal seals 284' and 286' as represented in the Figures. The invention is also applicable to such a core wrap.

The top layer 16 and the bottom layer 16' may be made from the same base substrate material which has been differently treated. Such nonwoven substrate may have a basis weight within a range of from about 8 to about 12 gsm. The top layer may be typically a nonwoven layer made of synthetic fibers that has been treated with a surfactant to increase its hydrophilicity. Both layers may in particular each comprises or consists of a nonwoven web, such as a carded nonwoven, a spunbond nonwoven ("S") or a meltblown nonwoven ("M"), and a multi-layer of any of these. For example, spunbond/meltblown laminate (spunmelt) polypropylene nonwovens are commonly used and are particularly suitable, especially those having a multi-layer SMS, or SMMS, or SSMMS, structure. Examples are disclosed in U.S. Pat. No. 7,744,576, US2011/0268932A1, US2011/0319848A1 or US2011/0250413A1. Typical material used to make the synthetic fibers are PE (polyethylene), PET (polyethylene terephthalate) and in particular PP (polypropylene).

Spunbond, also called spunlaid, nonwovens are made in one continuous process. Fibers are spun through a number of small orifices in a spinneret to form fibers or filaments, which are then directly dispersed into a web by deflectors or can be directed with air streams on a moving foraminous surface, such as a wire mesh conveyor. Meltblown nonwovens are produced by extruding melted polymer fibers through a spinneret or die consisting of up to 40 holes per inch to form long thin fibers which are stretched and cooled by passing hot air over the fibers as they fall from the die. The diameters of the fiber are significantly reduced by hot air which also breaks the continuous filaments into microfibers of varying length to diameter ratio. The extremely fine fibers (typically polypropylene) differ from other extrusions, particularly spunbond, in that they have low intrinsic strength but much smaller size offering key properties.

The spunbond process can be combined with the meltblown process to form a multi-layer web having S (spunbond) layer and M (meltblown) layer, in particular SM, SMS or SMMS webs, which are strong and offer the intrinsic benefits of fine fibers. The nonwovens may be consolidated using known techniques, typically thermal point bonding. In thermal point bonding, heat is applied locally on individual regions of the nonwoven to locally melt and fuse the fibers together. Fusion bond patterns are for example disclosed in US 2011/0250413 (Hu et al.) and US2014/0072767A1 (Klaska et al.). The resultant web is typically collected into rolls at the supplier and subsequently converted to finished products.

Core Channels

The absorbent core 28 may comprise one or more channels 26, in particular at least one channel on each side of the core's longitudinal centerline, which may or may not be connected and are present within the absorbent material layer. The channels may in particular be areas substantially free of absorbent material, in particular areas completely free of absorbent material (accidental minute amount of absorbent material due to involuntary contamination of the channels due to the high speed of the making process being disregarded).

The channels 26 may comprise a channel bond 27 between the top side 16 of the core wrap and the bottom side 16' of the core wrap. This bond 27 provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO2012/170798A1 (Jackels et al.), EP2,905,000 (Jackels et al.) and EP2,905,001 (Armstrong-Ostle et al.).

The hotmelt composition of the invention may be used to make these channel bonds 27, in addition or alternatively to the core perimeter bonds 280'-286'. Typically, the bonds 27 may generally have the same outline and shape as the channel areas 26 in which they are contained, but may be slightly smaller to allow for a safety margin (e.g., by a few mm) as some deviations from the optimal registration may happen during high speed process. It is expected that the channel bonds 27 may be more efficiently made and stronger if they are provided in macroscopic areas with no absorbent material (except of course accidental contamination) compared to bonds provided in areas containing non-negligible absorbent material.

Backsheet

The backsheet 25 is the liquid impermeable layer that generally form the garment-facing side of the absorbent article. The backsheet 25 prevents, or at least inhibits, the bodily exudates absorbed and contained in the absorbent core 28 from soiling articles such as bedsheets, undergarments, and/or clothing. The backsheet typically comprises a liquid impermeable, or at least substantially liquid impermeable layer, typically a plastic film having a thickness of about 0.01 mm to about 0.05 mm. Suitable backsheet materials also include breathable materials which permit vapors to escape from the absorbent article, while still preventing, or at least inhibiting, bodily exudates from passing through the backsheet.

The backsheet 25 is typically a laminate comprising a plastic film and on its external side a nonwoven outer cover for improving the overall feel of the backsheet. The outer cover nonwoven (sometimes referred to as a backsheet nonwoven) is joined to and covers the backsheet film. Thus, the outer cover material typically forms at least a portion of the garment-facing surface of the absorbent article 20. The outer cover material may comprise a bond pattern, apertures, and/or three-dimensional features.

Landing Zone

Referring to FIGS. 1 and 2, the absorbent article 20 in the form of a taped diaper may have a discrete landing zone 44 on its garment-facing side, typically disposed proximate the front edge 10 of the article 20. The landing zone 44 is configured to receive the fasteners 42 and may comprise, for example, a plurality of loops configured to be engaged with, a plurality of hooks on the fasteners 46, or vice versa.

The landing zone 44 typically comprises one or more discrete nonwoven materials that are attached to a portion of the outer cover material 40 in the front waist region 12. The present invention is in particular applicable to the bond area between such a landing zone and the backsheet.

Pant Diaper

The absorbent article may also be in the form of a pant having permanent or refastenable side seams, which is not represented herein but for which the invention may also apply. Pant articles comprising refastenable seams are for example disclosed in US2014/0005020 and U.S. Pat. No. 9,421,137. Typical pant articles comprise a chassis (sometimes referred to as a central chassis or central panel) comprising a topsheet, a backsheet, and an absorbent core, which may be as disclosed herein, and a front belt that defines a front waist region and a back belt that defines a back waist region. The chassis may be joined to a wearer-facing surface of the front and back belts or to a garment-facing surface of the belts. Side edges of the front belt may be joined to side edges of the back belt to form two side seams. The side seams may be any suitable seams known to those of skill in the art, such as butt seams or overlap seams, for example. When the side seams are permanently formed or refastenably closed, the absorbent article in the form of a pant has two leg openings and a waist opening circumference. The side seams may be permanently joined using adhesives or bonds, for example, or may be refastenably closed using hook and loop fasteners, for example.

Alternatively, instead of attaching belts to the chassis to form a pant, discrete side panels may be attached to side edges of the chassis. Suitable forms of pants comprising discrete side panels are disclosed e.g., in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Bond Areas

The absorbent article comprises at least a bond area between a first substrate and a second substrate provided by the hotmelt composition disclosed herein. A hotmelt composition according to the invention is disposed within the bond area. The bond area may be continuous or discontinuous. The bond area may be between a) a first nonwoven and a second nonwoven (nonwoven-nonwoven bond) or b) a nonwoven and a plastic film (nonwoven-film bond). The hotmelt composition of the invention is particular useful for nonwoven-film bonds, but may also be used for nonwoven-nonwoven bonds.

The hotmelt composition is applied in molten state to the first or second substrate, the hotmelt composition is then contacted with the other substrate, preferably with at least some pressure being applied between the two substrates before the hotmelt composition solidifies to ensure that bonding takes place. The hotmelt composition may be applied on the nonwoven for nonwoven-film application, or to the film, or to both substrates.

The hotmelt compositions of the inventions are particularly useful to bond a film and a nonwoven. Typical absorbent articles comprise a backsheet film. The hotmelt adhesives of the invention may thus be used to bond the backsheet film to any adjacent nonwovens in the article, for example the backsheet film to the front ears 40 in a taped diaper 20, and/or the backsheet film to the backsheet nonwoven outer cover, and/or the backsheet film to the bottom layer 16' of the core wrap of the absorbent core, and/or the backsheet film to the topsheet nonwoven on the side edges of the article. Other film-nonwoven application may be for example the film component of a landing zone laminate 44 to the backsheet nonwoven outer cover 25.

The hotmelt composition may be applied by any known process, which may be contact (slot, bead, adhesive coating as disclosed in WO2014/085063A1, etc.) or non-contact (spraying with spiral or random pattern, including intermittent spray application etc.). The hotmelt composition may be applied by any commercial applicators such as Nordson's Summit® (spiral), Signature® or Rhythm® applicator system. The hotmelt composition may be applied in a contact process (e.g., slot coating) or non-contact process on the first or the second substrate or both substrates preferably at a line speed of more than 2 m/s, in particular of more than 3 m/s, or even of more than 4 m/s.

The hotmelt composition may be typically applied at a basis weight ranging from about 5 gsm to about 30 gsm, alternatively from about 8 gsm to about 25 gsm, between the two substrates in the areas to be bonded. The hotmelt composition may also be used to make nonwoven-nonwoven bonds, such as channel bonds 27 between the top side and the bottom side of the absorbent core, topsheet to acquisition layer bond, or acquisition layer to core wrap bond, or any other bonds not explicitly mentioned herein.

The hotmelt adhesive composition may hold the first substrate and the second substrate bonded together within the bond area on its own. Alternatively, the hotmelt composition may be supplemented by another bonding means, such as mechanical bonds or fusion bonds.

TEST METHODS

Peak Molecular Weight (Mp) Measurement Method

The peak molecular weight is determined using a gel permeation chromatography (GPC) method. GPC is a well-known method wherein polymers are separated according to molecular size, the largest molecule eluting first. The peak molecular weights referred to herein can be determined with gel permeation chromatography (GPC) using polystyrene calibration standards, such as is done according to ASTM D5296. The molecular weight of any polymer or unknown polymer measured using GPC so calibrated is the styrene equivalent molecular weight, which herein is defined as the "peak molecular weight". Suitable solvents and temperatures are employed with GPC in order to achieve adequate molecular weight separation and resolution.

Weight Average Molecular Weight (Mw)

The weight average molecular weight is measured according to DIN 55672.

Enthalpy of Crystallization Test Method

The Enthalpy of Crystallization Parameter of a hotmelt adhesive composition is determined using the Enthalpy of Crystallization Test Method, which consists of performing ASTM D3418-15 with the following additional guidance. Specimen(s) are preferably extracted from molded or pelleted raw material adhesive composition. If raw material is not available, specimen(s) of adhesive are extracted from bonds of interest in an absorbent article using techniques known to those of skill in the art. Dry nitrogen is used as the purge gas in the differential scanning calorimeter (DSC). The rate of increase of temperature in the DSC is 10° C./min, and the rate of decrease of temperature in the DSC is 1° C./min. The mass-normalized enthalpy of crystallization is calculated as specified in section 11.4 based on the curve corresponding to decreasing temperature (at 1° C./min) and is reported as the "Enthalpy of Crystallization" in units of joules per gram (J/g) to the nearest 0.1 J/g.

Viscosity Test Method

The Viscosity Test method consists of performing a shear flow ramp on a rotational rheometer (such as ARES-G2, TA Instruments, New Castle, DE, USA, or equivalent). The rheometer is operated in a cone and plate configuration with a stainless steel cone 40 mm in diameter and with 0.04 rad cone angle mounted as upper tooling and stainless steel plate 40 mm in diameter as bottom tooling. Further the rheometer needs to be capable of sample temperature control with a precision equal to or better than 0.5° C. over at least the range of 20° C. up to 200° C.

A measurement gap of 49 μm is used in the method. To compensate for thermal expansion of the tooling the actual gap is mapped. For any temperature setpoint of interest, the following procedure is used (typical temperature setpoints of interest in this method include, but are not limited to 150° C., 170° C., and 190° C.) The rheometer is heated to the required measurement temperature. After 10 minutes of equilibration time the actual gap is determined by a "zero gap" routine. Zeroing the sample gap requires lowering the upper tooling until it touches the lower tooling, and an axial force is detected by the rheometer which is at least greater than 2 N. At this point the gap value is set to zero.

For a viscosity measurement at any temperature setpoint of interest, the compensation for thermal expansion is first determined as described above. The polymer composition is introduced in the rheometer, the gap is set to 74 μm, excess protruding sample is trimmed, and the gap is then set to 49 μm. The sample is preheated for 2 minutes at the temperature setpoint of interest. The shear stress is then recorded at 11 different shear rates logarithmically spanning the decade ranging from 1 and 10 s$^{-1}$, namely at shear rates of 1.00, 1.26, 1.58, 2.00, 2.51, 3.16, 3.98, 5.01, 6.31, 7.94, and 10.00 s$^{-1}$.

Analysis

The data are plotted on log-log fashion with shear rate on the abscissa and shear stress on the ordinate (logarithmic scales). A linear fit is then performed. Starting at the high-shear-rate end of the range, at least six and as many consecutive points as possible are included such that an R2 value of 0.9 or greater results. If an R2 value of 0.9 cannot be achieved fitting only six points, the fit of the six points corresponding to the highest shear rates is accepted. The value of the slope is defined as the viscosity parameter, which is reported in millipascal seconds (mPa s) to the nearest hundred mPa s.

Oscillatory Rheometry Test Method

The Oscillatory Rheometry Test Method is used to measure the Storage Modulus G' and the Loss Modulus G" of a polymer composition. A controlled-strain rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 μm is initially used in the method. To compensate for thermal expansion of the tooling, the gap is set to 1000 μm, and a mapping of actual plate gap (as measured using a suitable standard test fluid) a function of temperature over the range −10° C. to 150° C. is performed. This mapping is then used throughout the determination of the Storage Modulus Parameter and the Loss Modulus Parameter.

The rheometer is heated to 150° C., the polymer composition is introduced in the rheometer, the gap is set to 1050 μm, excess protruding sample is trimmed, and the gap is then set to 1000 μm. The axial force control of the rheometer is set to 0 N and be maintained within ±0.1 N of force during the experiment, thereby thermal expansion/contraction of the sample itself is compensated by adjusting the gap in order to avoid overfilling or underfilling in addition to the abovementioned compensation of the tooling. The rheometer is then allowed to cool to 130° C., at which point the measurement commences with temperature ramped from 130° C. to −10° C. at a constant rate of cooling of 2° C./min (hot to cold temperature ramp). The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min (cold to hot temperature ramp). The applied strain amplitude is 0.1%, and the frequency of oscillation is 1 Hz (that is, one cycle per second). The resulting oscillatory stress is recorded.

From the first decreasing temperature ramp (hot to cold), the storage modulus G' and the loss modulus G" are calculated and recorded from 130° C. until −10° C. in 0.5° C. steps or smaller steps. These values are reported in Pascals (Pa) to the nearest 1 Pa. The storage modulus G' and the loss modulus G" are plotted both as y axis in a logarithmic scale against the temperature as x-axis in a linear scale. The single values of the temperature steps are connected to obtain a storage modulus curve G' and a loss modulus curve G" verse the temperature. The Cross Over temperature is the temperature where the loss modulus G" [Pa] and the storage Modus G' [Pa] become equal and thereby the lines are crossing in the plot. In case more than one Cross Over temperature can be determined in the decreasing temperature ramp (hot to cold), only the highest Cross Over temperature is reported. The Cross Over is reported to the nearest 1° C.

From the second increasing temperature ramp (cold to hot) the storage modulus G' is calculated and recorded at 37° C., and these values are reported in Mega Pascals (MPa) to the nearest 0.1 MPa as the "Storage Modulus at 37° C.".

Extensional Test Method

The Extensional Test Method is used to determine the Yield Stress and the Toughness for a specimen of a polymer composition. A thin film specimen formed of polymer composition is analyzed with a rotational rheometer fitted with a specialized fixture with counter rotating rollers, and the stress associated with extensional strain imparted is measured and recorded.

Instrumental Setup

A rotational rheometer (ARES G2, TA Instruments, New Castle, DE, USA, or equivalent) is fitted with a fixture that has counter rotating cylindrical rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

Approximately 6 g±2 g of the polymer composition is placed in a circular polytetrafluoroethane (PTFE) bowl with a flat bottom (diameter of 60 mm±2 mm) and introduced into a vacuum oven held at 170° C. After 15 minutes at ambient pressure, the pressure is lowered to 10 mbar, and the polymer composition is subsequently held at 170° C. and at 10 mbar for 45 minutes to remove air bubbles from the polymer composition. If 170° C. is insufficient to melt the polymer compositions a temperature 30±10° C. above the melting temperature of the polymer material composition is used. The polymer composition is removed from the vacuum oven and allowed to cool to ambient lab conditions (23±2° C.) for 90±30 minutes, at which point the polymer composition is removed from the PTFE bowl and placed between 2 sheets of siliconised paper (such as product number 114918, Mondi Group, Hilm, Austria, or equivalent). A metal shim 500±30 μm in thickness is used in the heated press as a spacer to obtain a film thickness of 500 μm when pressed with a heated press at 90° C. for 60 seconds at a pressure sufficient to form a polymeric film. If 90° C. is insufficient to press a uniform flat film, a temperature approximately 10±5° C. below the melting point of the sample material composition such that the sample material composition is in a semi-solid state is used. The film is stored at least 120 hours in the laboratory at 23±2° C. prior to testing. From the film individual specimens for measurement are punched with a sample cutter to the final specimen dimensions of 20.0 mm by 10.0 mm by 500 μm.

Measurement

To secure the specimen film to the cylinders of the EVF, the cylinders are heated to 50° C. for 90±30 s in the forced-convection oven of the rheometer. After opening the oven, the specimen of polymer composition is briefly pressed onto the cylinders of the EVF to secure it to the cylinder surfaces. The specimen is placed with its length perpendicular to the axis of rotation of the cylinders. For polymer compositions, which are very stiff and do not adhere to the cylinder surface, the EVF are heated to 80° C. for 90±30 s in the forced-convection oven of the rheometer. Then a small droplet (0.03±0.01 g) of an auxiliary hotmelt adhesive is applied to each cylinder. The used auxiliary adhesive should exhibit a high stiffness (G' at 23° C. and 1 Hz of the auxiliary adhesive greater than 10 MPa) to not interfere with the measurement. The specimen of polymer composition is quickly pressed on the auxiliary adhesive on the cylinders of the EVF to fix it to the cylinder surfaces. The specimen is placed perpendicular to the axis of rotation of the cylinders.

The specimen mounted on the EVF is then placed in the forced convection oven of the rheometer for thermal conditioning and is kept isothermal at 37±0.5° C. for 300±10 s. After this time has elapsed, the specimen is mechanically conditioned. To mechanically condition the specimen, the torque transducer is zeroed, and the sample is put under a pre-stretch rate of 0.001 $s^{-1}$ for 0.30 s and then allowed to relax for 60 s (in this method, all strain is expressed in terms of Hencky strain, also known as "true strain" or "logarithmic strain.").

The measurement is performed in the FCO oven at 37° C.±0.5° C. The strain rate extension for the measurement is 1 $s^{-1}$, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded, and the measurement performed again on a replicate specimen.

Analysis

For the extensional stress calculation, a constant volume is assumed. From the raw torque versus angular displacement data recorded by the rheometer, extensional stress (in megapascals, or MPa) versus Hencky strain data are calculated. The data are plotted in semilogarithmic fashion with Hencky strain on the abscissa (linear scale) and extensional stress on the ordinate (logarithmic scale). A linear range is sought in this plot. If a linear range above a strain of 0.3 can be identified and this range can be fit with a positive slope with an $R^2$ value of 0.98 or greater, the value of the fitted line at a Hencky strain of zero (that is, the y-intercept), is defined as the Yield Stress, which is reported in MPa to the nearest tenth of MPa. Otherwise, the maximum value of extensional stress recorded during the measurement is reported as the Yield Stress, again reported in MPa to the nearest tenth of MPa.

The extensional stress (MPa) versus Hencky strain data calculated above are again plotted, but this time in linear fashion with Hencky strain on the abscissa (linear axis) and extensional stress on the ordinate (linear axis). The integral of extensional stress with strain (that is, the area under the extensional stress curve as a function of strain) is calculated from a strain of zero to the strain at which the sample ruptured (or, in the case it did not rupture during the measurement, to a strain of 4.0) and is reported as the Toughness, which is reported in units of megajoules per cubic meter, or $MJ/m^3$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hotmelt composition comprising:
    a low molecular weight metallocene-catalyzed polymer having a peak molecular weight below 130,000 g/mol, wherein the peak molecular weight is measured according to the Peak Molecular Weight (Mp) Measurement Method;
    a high molecular weight polyolefin having a peak molecular weight of from about 130,000 g/mol to about 700,000 g/mol, according to the Peak Molecular Weight (Mp) Measurement Method;
    an amorphous polyolefin having an enthalpy of crystallization of less than 10 J/g, wherein the enthalpy of crystallization is measured according to the Enthalpy of Crystallization Test Method; and
    a tackifier;
    wherein the low molecular weight metallocene-catalyzed polymer comprises:
    a first low molecular weight metallocene-catalyzed propylene-ethylene copolymer having an enthalpy of crystallization below 20 J/g; and
    a second low molecular weight metallocene-catalyzed propylene-ethylene copolymer having an enthalpy of crystallization above 20 J/g.

2. The hotmelt composition according to claim 1, wherein the low molecular weight metallocene-catalyzed polymer is a propylene-based polymer.

3. The hotmelt composition according to claim 1, wherein the first low molecular weight metallocene propylene-ethylene copolymer has an enthalpy of crystallization ranging from about 5 J/g to about 15 J/g.

4. The hotmelt composition according to claim 3, wherein the second low molecular weight metallocene-catalyzed propylene-ethylene copolymer has an enthalpy of crystallization ranging from about 25 J/g to about 45 J/g.

5. The hotmelt composition according to claim 2, wherein the low molecular weight metallocene-catalyzed polymer consists of a single low molecular weight metallocene-catalyzed propylene-based polymer, having an enthalpy of crystallization in the range of from about 20 J/g to about 30 J/g and a peak molecular weight between 25,000 and 35,000 g/mol.

6. The hotmelt composition according to claim 1, wherein the high molecular weight polyolefin is a metallocene-catalyzed propylene-based polymer.

7. The hotmelt composition according to claim 6, wherein the high molecular weight metallocene-catalyzed propylene-based polymer is a propylene-ethylene copolymer comprising greater than 80% by weight of polypropylene units.

8. The hotmelt composition according to claim 1, wherein the high molecular weight polyolefin has a peak molecular weight ranging from about 130,000 g/mol to about 410,000 g/mol.

9. The hotmelt composition according to claim 1, wherein the high molecular weight polyolefin has a peak molecular weight ranging from about 150,000 g/mol to about 360,000 g/mol.

10. A hotmelt composition comprising:
   a low molecular weight metallocene-catalyzed polymer having a peak molecular weight below 130,000 g/mol, wherein the peak molecular weight is measured according to the Peak Molecular Weight (Mp) Measurement Method;
   a high molecular weight polyolefin having a peak molecular weight of from about 130,000 g/mol to about 700,000 g/mol, according to the Peak Molecular Weight (Mp) Measurement Method;
   an amorphous polyolefin having an enthalpy of crystallization of less than 10 J/g, wherein the enthalpy of crystallization is measured according to the Enthalpy of Crystallization Test Method; and
   a tackifier;
   wherein the amorphous polyolefin is a metallocene-catalyzed propylene-based polymer; wherein the amorphous polyolefin has a weight-average molecular weight Mw of less than about 10 000 g/mol, as measured by ISO 16014 and has a viscosity below 500 mPa·s at 170° C. as measured by the Viscosity Test Method described herein, and no melting point detectable by DSC.

11. The hotmelt composition according to claim 1, comprising by weight of the hotmelt composition:
   from about 10% to about 70% of the low molecular weight metallocene catalyzed polymer(s),
   from about 1% to about 20% of the high molecular weight polyolefin(s),
   from about 1% to about 30% of the amorphous polyolefin(s),
   from about 20% to about 70% of the tackifier(s).

12. The hotmelt composition according to claim 11, comprising by weight of the hotmelt composition:
   from about 30% to about 60% of the low molecular weight metallocene catalyzed polymer(s),
   from about 2% to about 15% of the high molecular weight polyolefin(s),
   from about 5% to about 25% of the amorphous polyolefin(s),
   from about 30% to about 60% of the tackifier(s).

13. The hotmelt composition according to claim 1, which comprises less than 10% by weight of a mineral oil.

14. The hotmelt composition according to claim 1, wherein the viscosity of the hotmelt composition at 170° C. is in the range from about 1,000 mPa·s to about 7,000 mPa·s, as measured according to the Viscosity Test Method.

15. The hotmelt composition according to claim 1, wherein the composition has one or more properties selected from the group below:
   a storage modulus (G') at 37° C. smaller than 9.5 MPa, as measured in the cold to hot temperature ramp by the Oscillatory Rheometry Test Method disclosed herein; and/or
   a Yield Stress at 37° C. smaller than 1.5 MPa, as measured by Extension Test Method disclosed herein; and/or
   a Toughness above 2 MJ/m$^3$, as measured by the Extension Test Method disclosed herein; and/or
   a Cross Over temperature below 70° C. as measured in the hot to cold temperature ramp according to the Oscillatory Rheometry Test Method disclosed herein.

16. An absorbent article comprising a first substrate and a second substrate, wherein the first substrate and the second substrate are at least partially bonded by the hotmelt composition according to claim 1, and wherein either a) the first substrate is a first nonwoven and the second substrate is a second nonwoven or b) the first substrate is a nonwoven and the second substrate is a plastic film.

17. A process for bonding a first substrate to a second substrate, the process comprising the steps of applying the hotmelt composition according to claim 1 at least on the first substrate or the second substrate by a contact applicator or a spray applicator, and then pressing the two substrates together before the hotmelt composition solidifies to create a bond between the two substrates.

18. The process according to claim 17, wherein the hotmelt composition is applied on the first or second substrate at a line speed of more than 2 m/s.

* * * * *